United States Patent
Zhao et al.

(10) Patent No.: US 12,162,897 B2
(45) Date of Patent: Dec. 10, 2024

(54) 1,4-SULFUR-BRIDGED POLYCYCLIC COMPOUNDS CONTAINING DIHYDROBENZOFURAN STRUCTURE, ITS PREPARATION METHOD AND APPLICATION THEREOF

(71) Applicant: Chengdu University, Chengdu (CN)

(72) Inventors: Jianqiang Zhao, Chengdu (CN); Shun Zhou, Chengdu (CN); Weicheng Yuan, Chengdu (CN); Yong You, Chengdu (CN); Zhenhua Wang, Chengdu (CN)

(*) Notice: Subject to any disclaimer, the term of this patent is extended or adjusted under 35 U.S.C. 154(b) by 0 days.

(21) Appl. No.: 17/786,470

(22) PCT Filed: Mar. 18, 2022

(86) PCT No.: PCT/CN2022/081576
§ 371 (c)(1),
(2) Date: Jun. 16, 2022

(87) PCT Pub. No.: WO2022/167002
PCT Pub. Date: Aug. 11, 2022

(65) Prior Publication Data
US 2024/0287099 A1    Aug. 29, 2024

(30) Foreign Application Priority Data
Jul. 19, 2021  (CN) .......................... 202110815705.9

(51) Int. Cl.
*C07D 513/18* (2006.01)
*A61K 31/429* (2006.01)

(52) U.S. Cl.
CPC .......... *C07D 513/18* (2013.01); *A61K 31/429* (2013.01)

(58) Field of Classification Search
CPC ........................... C07D 513/18; A61K 31/429
See application file for complete search history.

(56) References Cited

FOREIGN PATENT DOCUMENTS

CN    109369661 A    2/2019

*Primary Examiner* — Brenda L Coleman
(74) *Attorney, Agent, or Firm* — Novoclaims Patent Services LLC; Mei Lin Wong (57) ABSTRACT

The present invention discloses a 1,4-sulfur-bridged polycyclic compound containing dihydrobenzofuran structure which has a structural formula (I). A preparation method is also disclosed which includes the steps of: dissolving 2-nitrobenzofuran (II) and 5H-thiazolone (III) in an organic solvent; then adding molecular sieve and chiral catalyst, stirring and allowing reaction at room temperature under argon protection until the reaction is completed; and carrying out separation and purification to obtain a 1,4-sulfur-bridged polycyclic compound (I) containing dihydrobenzofuran structure. The polycyclic compounds of the present invention have a substructure of dihydrobenzofuran and 1,4-thiopiperidinone. The application of the compound for the preparation of antitumor drugs is also disclosed, which has a good potential value in antitumor drug research. The preparation method has the advantages of novelty, simplicity, simple operation, mild reaction conditions, high yield and high stereoselectivity, and etc.

8 Claims, 4 Drawing Sheets

1,4-SULFUR-BRIDGED POLYCYCLIC COMPOUNDS CONTAINING DIHYDROBENZOFURAN STRUCTURE, ITS PREPARATION METHOD AND APPLICATION THEREOF

CROSS REFERENCE OF RELATED APPLICATION

This is a non-provisional National Stage entry under 35 USC 371 of a PCT international application number PCT/CN2022/081576, international filing date Mar. 18, 2022, which claimed priority to a foreign application number 202110815705.9 filed on Jul. 19, 2021 in China (CN), the entire contents of each of which are expressly incorporated herein by reference.

BACKGROUND OF THE PRESENT INVENTION

Field of Invention

The present invention relates to a field of organic synthesis, and more particularly to a 1,4-sulfur-bridged polycyclic compounds containing a dihydrobenzofuran structure, a preparation method and application thereof.

Description of Related Arts

Bridged polycyclic compounds are commonly found in natural products and drug molecules, wherein the bridged polycyclic compounds have a wide range of biological activities, and are an important source for new drugs development. Morphine, as a clinically important potent analgesic, is one type of a bridged polycyclic aromatic drug with a dihydrobenzofuran structure. As the important biological activities of benzofuran structures and the extensive pharmacological properties of bridged polycyclic compounds, there is a great scientific significance for the synthesis of bridged polycyclic compounds containing dihydrobenzofuran structures. Meanwhile, in view of drug design, combining two or more pharmacodynamic functional groups into one molecule may produce unexpected biological activities, which has particularly important application value.

There is a practical difficulty for asymmetric dearomatization in the field of organic synthesis. At present, the major research direction is electron-rich aromatic compounds, such as indole, naphthol, etc., wherein it mainly uses their inherent nucleophilicity of these compounds. In recent years, organic chemists pay extensive attention to the asymmetric dearomatization of nitroheteroaromatics, such as nitroindole, nitrobenzofuran, and nitrothiophene. However, through literature research, it is found that the asymmetric reactions involving nitroheteroaromatic compounds are mainly used to construct chiral polycyclic fused compounds and chiral polycyclic spiro compounds. On the other hand, there are few reports for the construction of bridged polycyclic compounds. It is to the provision of a construction of bridged polycyclic compounds to enrich and screen compounds with good biological activity.

SUMMARY OF THE PRESENT INVENTION

One of the objects of the present invention is to provide a bridged polycyclic compounds containing dihydrobenzofuran structure to solve the above problems.

In order to achieve the above object, the present invention provides 1,4-sulfur-bridged polycyclic compounds containing dihydrobenzofuran structure which has a structural formula (I):

According to the above structural formula, Ar is various substituted aromatic rings, heteroaromatic rings, etc. R1 group is a single substituent or multiple substituents, wherein the substituent is selected from a group consisting of hydrogen, alkyl, alkoxy, nitro or halogen; R2 group is one of methyl, ethyl and benzyl.

The present invention first provides a new class of chiral bridged polycyclic compounds containing dihydrobenzofuran structure, wherein the compound has a substructure of dihydrobenzofuran and 1,4-thiopiperidinone to provide more therapeutic candidate molecules for new drug development and drug screening.

Figure 1:
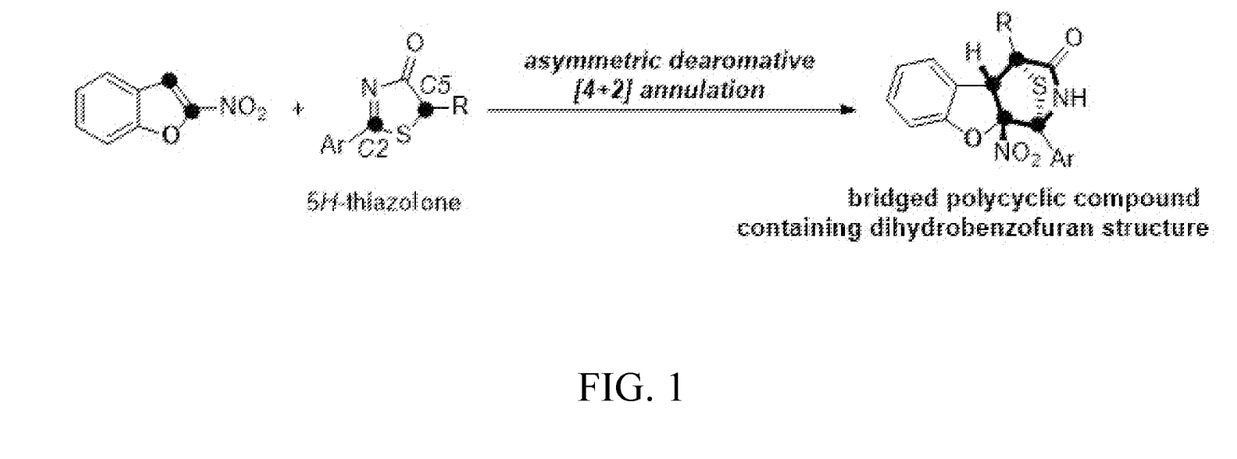
FIG. 1 is a diagram illustrating an asymmetric reaction structure of a nitroaromatic heterocycle according to a preferred embodiment of the present invention.

A second object of the present invention is to provide a preparation method of the above mentioned bridged polycyclic compounds containing dihydrobenzofuran structure, which comprises the steps of: dissolving 2-nitrobenzofuran (II) and 5H-thiazolone (III) in an organic solvent to form a first solution; adding molecular sieve and chiral catalyst into the first solution to form a second solution, stirring the second solution during a reaction thereof at room temperature under argon protection; and after the reaction is completed, obtaining a 1,4-sulfur-bridged polycyclic compounds (I) containing dihydrobenzofuran structure by separation and purification, wherein the 2-nitrobenzofuran (II) has a structure of:

wherein the 5H-thiazolone (III) has a structure of:

wherein its reaction formula is:

5H-thiazolone as a good sulfur-containing nucleophile is widely used in organic synthesis. However, the existing research mainly focuses on the nucleophilic addition reaction at the C5 position, wherein there are few reports on the construction of 1,4-sulfur-bridged rings using the nucleophilicity at the C5 position and the electrophilicity at the C2 position. Therefore, through a huge number of experiments, the present application selects a suitable catalytic system, uses the substrates 2-nitrobenzofuran and 5H-thiazolone to perform Michael addition first and then Mannich reaction, so as to construct the bridged polycyclic compounds with four consecutive chiral centers containing dihydrobenzofuran structures (FIG. 1) in one step manner.

According to the preferred embodiment, the solvent for reaction is selected from a group consisting of one or more of combinations of toluene, mesitylene, dichloromethane, chloroform, tetrahydrofuran, ether, acetonitrile, ethanol, methanol, and 1,4-dioxane, chlorobenzene.

Preferably, dichloromethane is selected because of the highest yield of the reaction and the best stereoselectivity.

According to the preferred embodiment, the chiral catalyst is a chiral tertiary amine-thiourea bifunctional catalyst or a chiral tertiary amine-squaramide bifunctional catalyst.

Preferably, the chiral tertiary amine-thiourea catalyst-chiral tertiary amine-squaramide catalyst has the structure of the following formula A or B or C or D, i.e. the catalyst used is preferably selected from one of the following:

Catalyst D is further preferred because of the high yield of the reaction and good stereoselectivity.

According to the preferred embodiment, the molar ratio of the reaction substrate is nII:nIII=2:1-1:2.

It is further preferred that the molar ratio of the reaction substrate is nII:nIII=1:1.3 since the reaction yield is higher.

A third object of the present invention is to provide the use of the above-mentioned compound for the preparation of antitumor drugs.

Specifically, the application value of the above-mentioned compounds of the present invention is that: preliminary cell activity experiments show that the compounds of the present invention can effectively kill the human leukemia cells K562 and human lung cancer cells A549. The cell activity research results are shown in Table 1. Therefore, through the further research, the compounds of the present invention are able to become the leading anti-tumor drugs.

Specific experimental operations: 5000 human leukemia cells K562 and human lung cancer cells A549 are seeded into 96-well cell culture plates respectively to grow for 24 hours. Then, a predetermined concentration of the above synthesized compounds are added respectively, wherein the antitumor drug cisplatin is used as a control for 48 hours. The mean 50% inhibitory concentration (IC50) of all compounds is then determined. Each concentration is repeated at least three times, and all experiments are repeated three times, and the average results obtained are shown in Table 1.

TABLE 1

Cell Viability Assay Results

| | $IC_{50}$ (uM)[a] | |
| --- | --- | --- |
| Compound | A549 | K562 |
| I-aa | 28.15 | 12.4 |
| I-ba | 32.58 | 13.02 |
| I-ca | 57.72 | 18.97 |
| I-da | 34.29 | 10.27 |
| I-ea | 45.33 | 21.42 |
| I-fa | 67.59 | 30.87 |
| I-ga | 30.84 | 7.09 |
| I-ha | 67.32 | 22.27 |
| I-ia | 33.26 | 14.54 |
| I-ja | 4.83 | 2.60 |
| I-ka | 33.00 | 29.62 |
| I-la | 15.61 | 3.10 |
| I-ab | 57.00 | 52.19 |
| I-ac | 58.23 | 74.61 |
| I-ad | 39.95 | 50.23 |

TABLE 1-continued

Cell Viability Assay Results

| | $IC_{50}$ (uM)[a] | |
|---|---|---|
| Compound | A549 | K562 |
| I-ae | 45.51 | 54.74 |
| I-af | 39.50 | 46.39 |
| I-ag | 44.60 | 30.21 |
| I-ah | 20.46 | 59.39 |
| I-ai | 23.88 | 32.32 |
| Cisplatin | 23.96 | 20.33 |

As shown in Table 1, the compounds of the present invention have comparable or even better inhibitory effects on the activities of K562 and A549 than cisplatin.

Comparing to the prior art, the advantages of the present invention are that: through the asymmetrical dearomatization [4+2] reaction of 2-nitrobenzofuran, a series of bridged polycyclic compounds containing both dihydrobenzofuran and 1,4-thio-piperidinone substructures are firstly disclosed. These compounds have four consecutive chiral centers and contain easily functionalized groups, which are convenient for derivatization and synthesis of other chiral polycyclic compounds. Meanwhile, the preliminary cell activity studies show that these compounds have a good inhibitory effect on human leukemia cell K562 and human lung cancer cell A549, such that the compounds are able to become the leading anti-tumor drugs. Moreover, the method of the present invention has the advantages of mild reaction conditions, readily available raw materials and catalysts, simple operation, exceptionally good stereoselectivity (>20:1 dr, 98% ee), and etc.

DETAILED DESCRIPTION OF THE PREFERRED EMBODIMENT

The following description in conjunction with the accompanying drawings is further disclosed.

The raw materials, solvents, catalysts, molecular sieves, etc. disclosed in the present invention are all commercially available.

Example 1: Synthetic Compound I-aa

Add 0.2 mmol of 2-nitrobenzofuran II-a, 0.26 mmol of 5H-thiazolone III-a, 100 mg of 5A molecular sieve and chiral catalyst A/B/C/D into a dry test tube. Then, add 2.0 mL of solvent, and the reaction is carried out at room temperature under argon protection. After the reaction is completed, the crude product is separated and purified by column chromatography to obtain compound I-aa, wherein different reaction conditions are as shown in Table 2, and the concrete reaction process is as follows:

TABLE 2

Different reaction conditions

| SN | Catalyst | x | Solvent | Time (h) | Molecular Sieve | Ar | Yield (%) | dr | ee (%) |
|---|---|---|---|---|---|---|---|---|---|
| 1 | A | 20 | CHCl$_3$ | 20 | No | No | 40 | >20:1 | 73 |
| 2 | B | 20 | CHCl$_3$ | 20 | No | No | 41 | >20:1 | 61 |
| 3 | C | 20 | CHCl$_3$ | 10 | No | No | 39 | >20:1 | 64 |
| 4 | D | 20 | CHCl$_3$ | 24 | No | No | 33 | >20:1 | 85 |
| 5 | D | 20 | CH$_2$Cl$_2$ | 24 | No | No | 31 | >20:1 | 93 |
| 6 | D | 20 | (CH$_2$Cl)$_2$ | 24 | No | No | 30 | >20:1 | 93 |
| 7 | D | 20 | CH$_2$Cl$_2$ | 24 | Yes | No | 60 | >20:1 | 91 |
| 8 | D | 20 | CH$_2$Cl$_2$ | 24 | Yes | Yes | 85 | >20:1 | 94 |
| 9 | D | 10 | CH$_2$Cl$_2$ | 48 | Yes | Yes | 83 | >20:1 | 94 |
| 10 | D | 5 | CH$_2$Cl$_2$ | 72 | Yes | Yes | 78 | >20:1 | 93 |

In Table 1, "X" represents the molar percentage of the catalyst being used.

As shown in Table 1, it is preferred that 20 mol % of catalyst D, dichloromethane as solvent, adding molecular sieve additive are preferred for reaction under argon protection.

The obtained compound I-aa is a white solid with a purity of >99% detected by HPLC; >20:1 dr, 94% ee; $[\alpha]_D^{20}$=−182.6 (c 1.0, CH2Cl2); m.p. 163.1-164.0° C.

Wherein, the ee value is determined by HPLC method: Chiralpak IC column; mobile phase 90/10 hexane/EtOH; flow rate: 1.0 mL/min; detection wavelength λ=220 nm; retention time $t_{major}$=15.79 min, $t_{minor}$=10.01 min.

Structure identification: $^1$H NMR (300 MHz, DMSO-d$_6$) δ 10.20 (s, 1H), 7.62-7.53 (m, 2H), 7.53-7.44 (m, 4H), 7.44-7.34 (m, 1H), 7.23-7.10 (m, 2H), 4.81 (s, 1H), 1.60 (s, 3H). $^{13}$C NMR (75 MHz, DMSO-d$_6$) δ 206.1, 176.2, 160.0, 130.4, 129.9, 129.2, 128.7, 127.1, 126.1, 125.8, 123.2, 123.0, 110.3, 81.6, 62.5, 59.5, 11.8. HRMS (ESI-TOF) Calcd. for C$_{18}$H$_{15}$N$_2$O$_4$S [M+H]$^+$: 355.0747; found: 355.0747.

Figure 4:
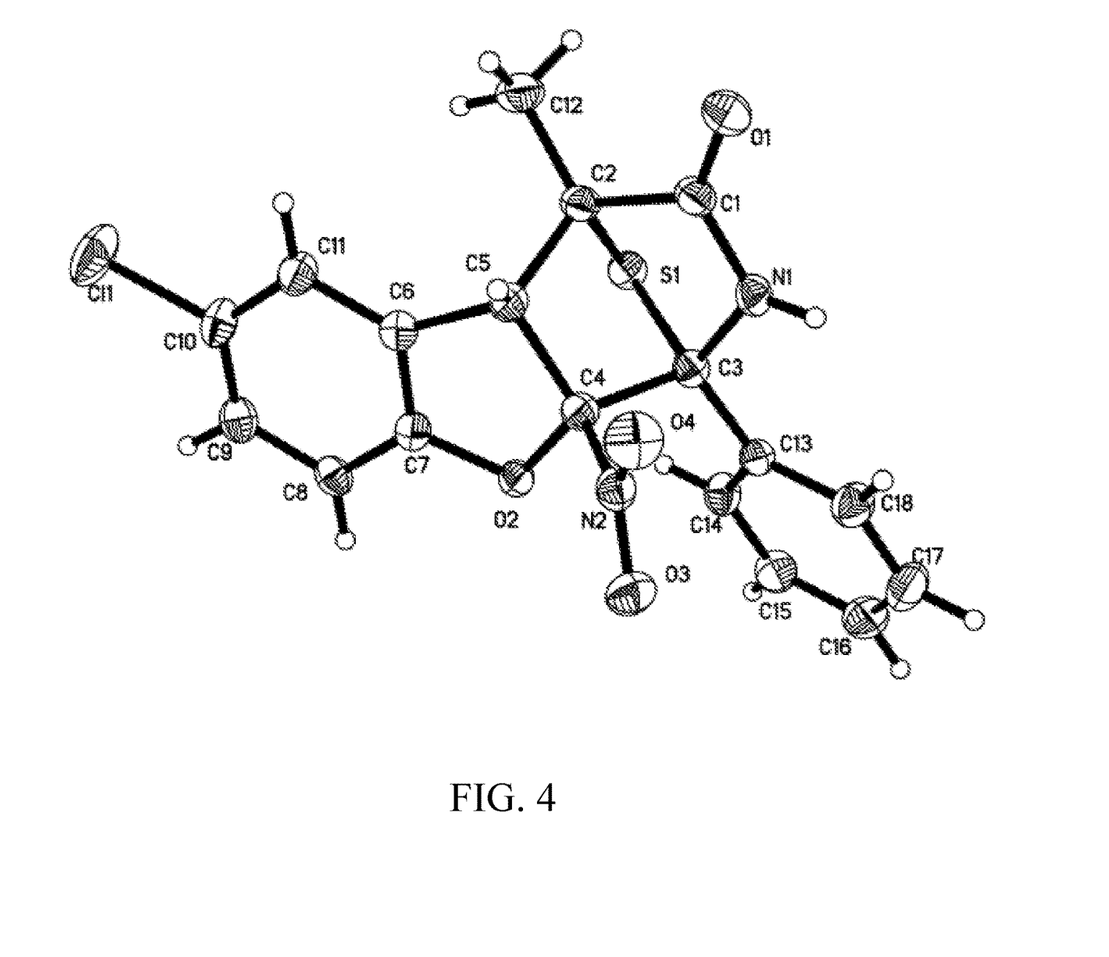
FIG. 4 illustrates a single crystal diagram of the I-ea prepared in Example 5.

The measurement results are shown in FIG. 4, indicating that the absolute configuration of compound I-ea is (C2R, C15S, C16S, C17R). By analogy, the compounds of the present invention are all in this configuration.

Example 2: Synthetic Compound I-ba

Add 0.2 mmol of 2-nitrobenzofuran II-b, 0.26 mmol of 5H-thiazolone III-a, 5A 100 mg of molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ba.

Pale yellow solid; 87% yield; >20:1 dr, 94% ee; m.p. 178.5-179.5° C., $[\alpha]_D^{25}$=−425.5 (c 1.0, CH$_2$Cl$_2$).

Wherein, the ee value is determined by HPLC method: Chiralpak IC column; mobile phase 95/5 hexane/EtOH; flow rate: 1.0 mL/min; detection wavelength λ=220 nm; $t_{major}$=21.78 min, $t_{minor}$=12.01 min.

Structural identification: $^1$H NMR (400 MHZ, DMSO-d$_6$) δ 10.23 (s, 1H), 7.59-7.53 (m, 2H), 7.51-7.45 (m, 3H), 7.37 (dd, J=8.1, 2.4 Hz, 1H), 7.26-7.18 (m, 2H), 4.83 (s, 1H), 1.61 (s, 3H). $^{13}$C NMR (101 MHz, DMSO-d$_6$) δ 176.5, 159.6, 157.2, 156.7, 130.5, 129.1, 128.1 (d, J=266.6 Hz, 1C), 127.6, 125.3 (d, J=9.1 Hz, 1C), 117.3 (d, J=25.2 Hz, 1C), 113.7 (d, J=26.3 Hz, 1C), 111.6 (d, J=9.0 Hz, 1C), 82.1, 62.8, 60.0, 12.3. HRMS (ESI-TOF) Calcd. for C$_{18}$H$_{13}$FN$_2$NaO4S [M+Na]$^+$: 395.0472; found: 395.0466.

Example 3: Synthetic Compound I-ca

Add 0.2 mmol of 2-nitrobenzofuran II-c, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ca.

Pale yellow solid; 95% yield; >20:1 dr, 90% ee; m.p. 138.2-139.1° C., $[\alpha]_D^{25}$=−538.6 (c 1.0, CH$_2$Cl$_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=23.51 min, $t_{minor}$=14.52 min.

Structure identification: $^1$H NMR (400 MHZ, DMSO-d$_6$) δ 10.28 (s, 1H), 7.58 (dd, J=6.8, 3.0 Hz, 2H), 7.55-7.47 (m, 3H), 7.43-7.29 (m, 2H), 7.21-7.11 (m, 1H), 4.94 (s, 1H), 1.61 (s, 3H). $^{13}$C NMR (101 MHZ, DMSO-d$_6$) δ 176.4, 146.7 (d, J=11.1 Hz, 1C) 146.5 (d, J=247.4 Hz, 1C), 130.6, 129.2, 127.5, 127.4, 126.6, 124.5 (d, J=5.0 Hz, 1C), 122.4, 122.3, 117.9 (d, J=16.2 Hz, 1C), 82.2, 62.9, 60.4, 55.4, 12.3. HRMS (ESI-TOF) Calcd. for C$_{18}$H$_{13}$FN$_2$NaO$_4$S [M+Na]$^+$: 395.0472; found: 395.0465.

Example 4: Synthetic Compound I-da

Add 0.2 mmol of 2-nitrobenzofuran II-d, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-da.

Pale yellow solid; 90% yield; >20:1 dr, 84% ee; m.p. 144.3-145.2° C., $[\alpha]_D^{25}$=−345.6 (c 1.0, $CH_2Cl_2$).

Wherein, the ee value is determined by HPLC method: Chiralpak IC column; mobile phase 95/5 hexane/$^i$Pr—OH; flow rate: 1.0 mL/min; detection wavelength λ=220 nm; $t_{major}$=9.46 min, $t_{minor}$=7.60 min.

Structure identification: $^1$H NMR (400 MHZ, DMSO-$d_6$) δ 10.34 (s, 1H), 7.60-7.54 (m, 2H), 7.54-7.48 (m, 3H), 7.47-7.41 (m, 1H), 7.22 (dd, J=11.6, 8.1 Hz, 2H), 4.86 (s, 1H), 1.66 (s, 3H). $_{13}$C NMR (101 MHz, DMSO-$d_6$) δ 176.2, 161.4, 132.7, 130.8, 130.6, 129.2, 129.1, 127.6, 125.7, 124.5, 122.4, 110.1, 81.9, 64.8, 60.1, 14.8. HRMS (ESI-TOF) Calcd. for $C_{18}H_{13}ClN_2NaO_4S$ [M+Na]$^+$: 411.0177; found: 411.0159.

Example 5: Synthetic Compound I-ea

Add 0.2 mmol of 2-nitrobenzofuran II-e, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ea.

White solid; 90% yield; >20:1 dr, 93% ee; m.p. 155.3-156.2° C., $[\alpha]_D^{25}$=−419.1 (c 1.0, $CH_2Cl_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=11.11 min, $t_{minor}$=7.89 min.

Figure 2:
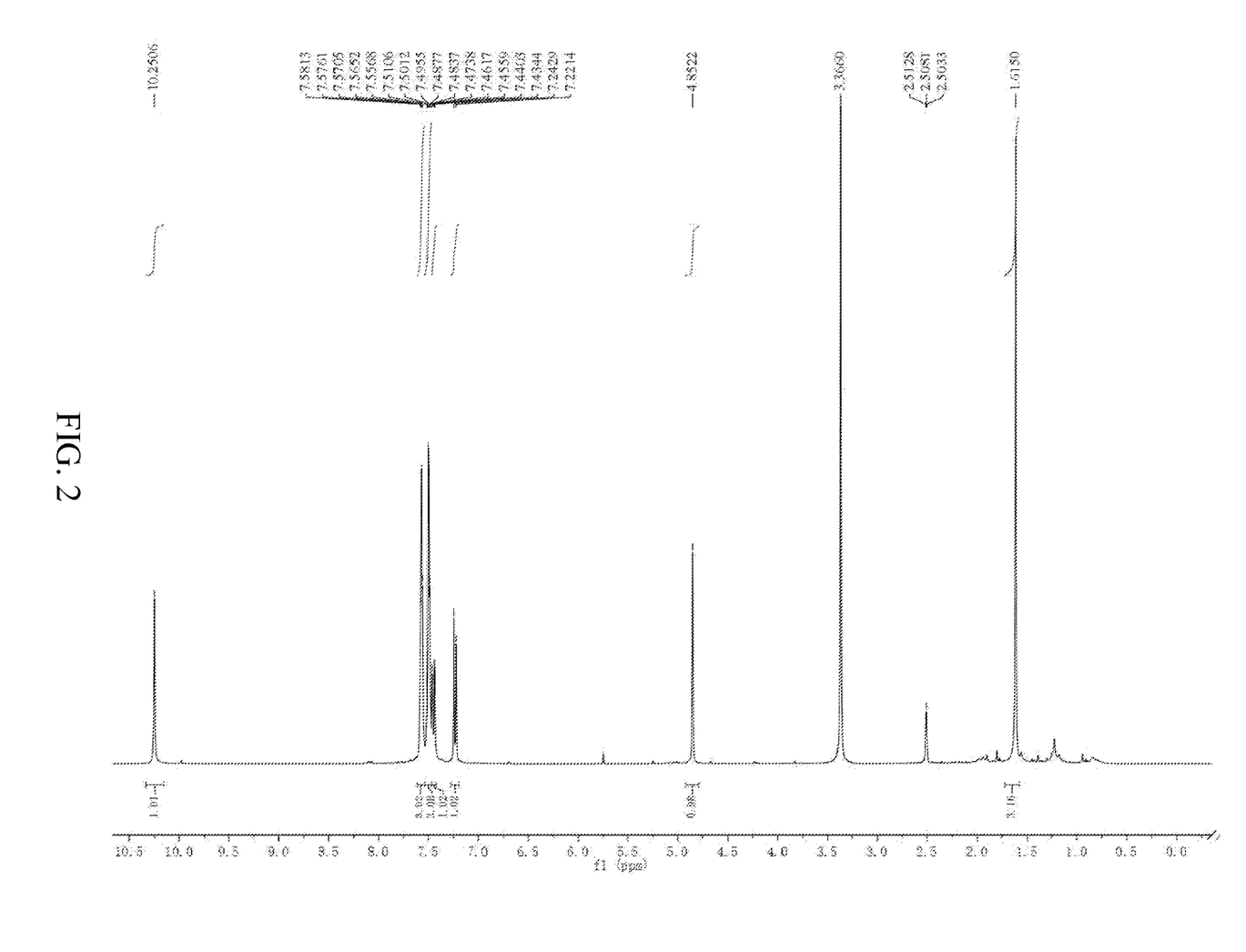
FIG. 2 illustrates a hydrogen spectrogram of the I-ea obtained in Example 5.
Figure 3:
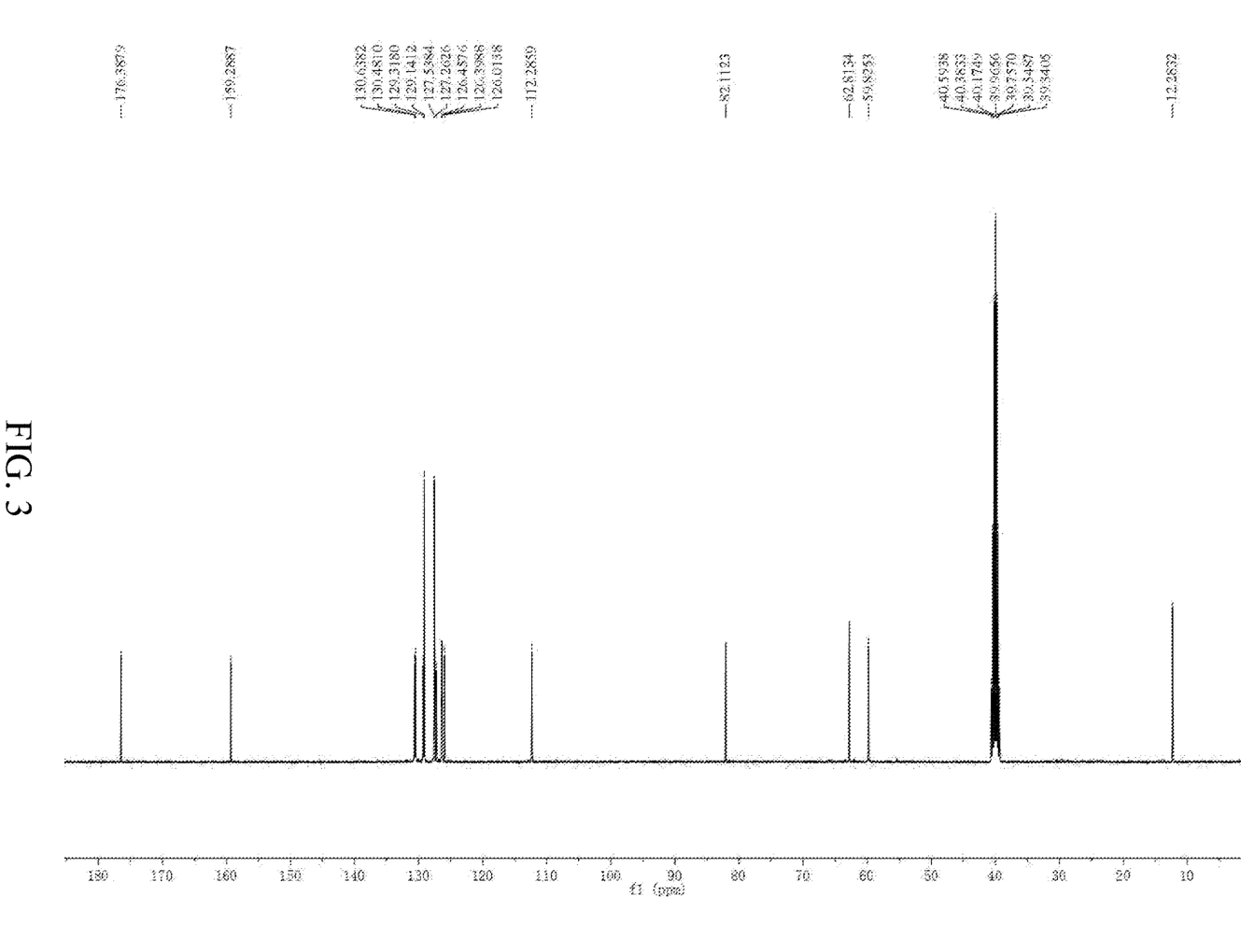
FIG. 3 illustrates a carbon spectrogram of the I-ea prepared in Example 5.

Structure identification: $^1$H NMR (400 MHZ, DMSO-$d_6$) (shown in FIG. 2) δ 10.25 (s, 1H), 7.61-7.54 (m, 3H), 7.53-7.47 (m, 3H), 7.45 (dd, J=8.6, 2.3 Hz, 1H), 7.23 (d, J=8.6 Hz, 1H), 4.85 (s, 1H), 1.62 (s, 3H). $^{13}$C NMR (101 MHz, DMSO-$d_6$) (shown in FIG. 3) δ 176.4, 159.3, 130.7, 130.5, 129.3, 129.2, 127.5, 127.3, 126.5, 126.4, 126.0, 112.3, 82.1, 62.8, 59.8, 12.3. HRMS (ESI-TOF) Calcd. for $C_{18}H_{13}ClN_2NaO_4S$ [M+Na]$^+$: 411.0177; found: 411.0161.

Single Crystal Diffraction Experiment

Single crystal cultivation: The main component compound I-ea (40 mg) obtained in Example 5 is dissolved in 20 mL of a mixture of dichloromethane and ethanol ($V_{dichloromethane}$:$V_{dichloromethane}$=1:10). After resting at room temperature for 7 days, a single crystal is precipitated, and the single crystal is collected for single crystal diffraction test. The test parameters are shown in Table 3.

TABLE 3

| Single crystal test parameters | |
|---|---|
| Identification code | I-ea |
| Empirical formula | $C_{20}H_{19}ClN_2O_5S_2$ |
| Formula weight | 466.94 |
| Temperature/K | 293(2) |
| Crystal system | monoclinic |
| Space group | C2 |
| a/Å | 26.7417(6) |
| b/Å | 6.38250(16) |
| c/Å | 12.8324(3) |
| α/° | 90 |
| β/° | 103.440(2) |
| γ/° | 90 |
| Volume/Å$^3$ | 2130.24(9) |
| Z | 4 |
| $ρ_{calc}$ g/cm$^3$ | 1.456 |
| μ/mm$^{-1}$ | 3.728 |
| F(000) | 968.0 |
| Crystal size/mm$^3$ | 0.17 × 0.12 × 0.09 |
| Radiation | CuKα (λ = 1.54184) |
| 2Θrange for data collection/° | 6.796 to 134.108 |
| Index ranges | −28 ≤ h ≤ 31, −7 ≤ k ≤7, −15 ≤ l ≤ 15 |
| Reflections collected | 7977 |
| Independent reflections | 3813 [$R_{int}$ = 0.0320, $R_{sigma}$ = 0.0422] |
| Data/restraints/parameters | 3813/1/278 |
| Goodness-of-fit on F$^2$ | 1.027 |
| Final R indexes [I >= 2σ (I)] | R1 = 0.0425, wR2 = 0.1083 |
| Final R indexes [all data] | R1 = 0.0462, wR2 = 0.1133 |
| Largest diff. peak/hole/e Å$^{-3}$ | 0.23/−0.46 |
| Flack parameter | 0.001(14) |

The measurement results are shown in FIG. 4, indicating that the absolute configuration of compound I-ea is (C2S, C3R, C4R, C5S). By analogy, the compounds of the present invention are all in this configuration.

Example 6: Synthetic Compound I-fa

Add 0.2 mmol of 2-nitrobenzofuran II-f, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-fa.

White solid; 86% yield; >20:1 dr, 92% ee; m.p. 149.3-150.3° C., $[\alpha]_D^{25}$=−444.4 (c 1.0, $CH_2Cl_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=10.66 min, $t_{minor}$=8.61 min.

Structure identification: $^1$H NMR (400 MHZ, DMSO-d6) δ 10.25 (s, 1H), 7.68 (d, J=2.1 Hz, 1H), 7.61-7.54 (m, 3H), 7.53-7.45 (m, 3H), 7.18 (d, J=8.6 Hz, 1H), 4.86 (s, 1H), 1.61 (s, 3H). $^{13}$C NMR (101 MHz, DMSO-$d_6$) δ 176.4, 159.8, 133.5, 130.5, 129.3, 129.2, 129.1, 127.6, 126.5, 126.4, 114.9, 112.8, 82.1, 62.8, 59.8, 12.3. HRMS (ESI-TOF) Calcd. for $C_{18}H_{13}{}^{79}BrN_2NaO_4S$ [M+Na]$^+$: 454.9672; found: 454.9653; For $C_{18}H_{13}{}^{81}BrN_2NaO_4S$ [M+Na]$^+$: 456.9651; found: 454.9630.

Example 7: Synthetic Compound I-ga

Add 0.2 mmol of 2-nitrobenzofuran II-g, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ga.

White solid; 86% yield; >20:1 dr, 92% ee; m.p. 161.8-162.8° C., [60]$_D{}^{25}$=−597.1 (c 1.0, $CH_2Cl_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=28.17 min, $t_{minor}$=15.67 min.

Structural identification: $^1$H NMR (400 MHZ, DMSO-d$_6$) δ 10.24 (s, 1H), 7.60-7.54 (m, 2H), 7.53-7.47 (m, 4H), 7.43 (d, J=8.1 Hz, 1H), 7.35 (dd, J=8.0, 1.8 Hz, 1H), 4.81 (s, 1H), 1.59 (s, 3H). $^{13}$C NMR (101 MHz, DMSO-d$_6$) δ 176.4, 161.2, 130.5, 129.3, 129.1, 128.0, 127.6, 126.5, 126.4, 123.5, 123.0, 114.1, 82.1, 62.8, 59.5, 12.2. HRMS (ESI-TOF) Calcd. for $C_{18}H_{13}{}^{79}BrN_2NaO_4S$ [M+Na]$^+$: 454.9672; found: 454.9662; For $C_{18}H_{13}{}^{81}BrN_2NaO_4S$ [M+Na]$^+$: 456.9651; found: 454.9642.

Example 8: Synthetic Compound I-ha

Add 0.2 mmol of 2-nitrobenzofuran II-h, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ha.

Yellow solid; 80% yield; >20:1 dr, 88% ee; m.p. 222.8-223.5° C., [α]$_D{}^{25}$=−47.9 (c 0.5, $CH_2Cl_2$).

Accordingly, the ee value is determined by HPLC method: Chiralpak IC column; mobile phase 70/30 hexane/EtOH; flow rate: 1.0 mL/min; detection wavelength λ=220 nm; $t_{major}$=9.73 min, $t_{minor}$=10.65 min.

Structural identification: $^1$H NMR (400 MHZ, DMSO-d$_6$) δ 10.33 (s, 1H), 8.43-8.27 (m, 2H), 7.58-7.54 (m, 2H), 7.54-7.48 (m, 3H), 7.45 (d, J=8.9 Hz, 1H), 5.75 (s, 1H), 1.66 (s, 3H). $^{13}$C NMR (101 MHZ, DMSO-d$_6$) δ 176.2, 164.8, 143.8, 130.7, 129.7, 129.2, 129.0, 128.4, 127.7, 127.5, 126.7, 125.9, 122.6, 111.4, 82.3, 62.9, 59.2, 12.1. HRMS (ESI-TOF) Calcd. for $C_{18}H_{13}N_3NaO_6S$ [M+Na]$^+$: 422.0417; found: 422.0403.

Example 9: Synthetic Compound I-ia

Add 0.2 mmol of 2-nitrobenzofuran II-i, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ia.

White solid; 78% yield; >20:1 dr, 89% ee; m.p. 140.2-140.9° C., [α]$_D{}^{25}$=−284.3 (c 1.0, $CH_2Cl_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=10.12 min, $t_{minor}$=7.33 min.

Structure identification: $^1$H NMR (400 MHZ, DMSO-d$_6$) δ 10.18 (s, 1H), 7.58 (dd, J=6.8, 3.0 Hz, 2H), 7.53-7.45 (m, 3H), 7.35 (d, J=7.7 Hz, 1H), 7.01 (s, 1H), 6.96 (d, J=7.7 Hz, 1H), 4.74 (s, 1H), 2.34 (s, 3H), 1.58 (s, 3H). $^{13}$C NMR (101 MHz, DMSO-d$_6$) δ 176.7, 160.8, 141.0, 130.4, 129.7, 129.1, 127.5, 126.5, 126.1, 124.1, 120.7, 111.2, 82.0, 63.0, 59.8, 21.6, 12.3. HRMS (ESI-TOF) Calcd. for $C_{19}H_{16}N_2NaO_4S$ [M+Na]$^+$: 391.0723; found: 391.0710.

Example 10: Synthetic Compound I-ja

Add 0.2 mmol of 2-nitrobenzofuran II-j, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ja.

White solid; 78% yield; >20:1 dr, 88% ee; m.p. 188.7-189.5° C., $[\alpha]_D^{25}$=−219.5 (c 1.0, $CH_2Cl_2$).

Accordingly, the ee value is determined by HPLC method: Chiralpak IC column; mobile phase 90/10 hexane/EtOH; flow rate: 1.0 mL/min; detection wavelength $\lambda$=220 nm; $t_{major}$=12.69 min, $t_{minor}$=9.04 min.

Structure identification: $^1$H NMR (400 MHZ, DMSO-$d_6$)δ 10.16 (s, 1H), 7.57 (dd, J=6.8, 3.0 Hz, 2H), 7.52-7.46 (m, 3H), 7.35 (d, J=8.4 Hz, 1H), 6.84 (d, J=2.3 Hz, 1H), 6.70 (dd, J=8.4, 2.3 Hz, 1H), 4.70 (s, 1H), 3.78 (s, 3H), 1.57 (s, 3H). $^{13}$C NMR (101 MHz, DMSO-$d_6$) δ 176.7, 162.0, 161.8, 130.4, 129.6, 129.1, 127.5, 127.0, 126.7, 115.2, 109.7, 97.0, 81.9, 63.1, 59.6, 56.2, 12.2. HRMS (ESI-TOF) Calcd. for $C_{19}H_{16}N_2NaO_5S$ [M+Na]$^+$: 407.0672; found: 407.0656.

Example 11: Synthetic Compound I-ka

Add 0.2 mmol of 2-nitrobenzofuran II-k, 0.26 mmol of 5H-thiazolone III-a, 100 mg of 5A molecular sieve and 0.02 mmol of chiral catalyst D into a dry test tube. Then, add 2.0 mL of dichloride Methane, wherein the reaction is carried out at room temperature under argon protection. After the reaction is complete, the crude product is separated and purified by column chromatography to obtain compound I-ka.

White solid; 70% yield; >20:1 dr, 89% ee; m.p. 177.4-178.3° C., $[\alpha]_D^{25}$=−214.1 (c 1.0, $CH_2Cl_2$).

Wherein, the ee value is determined by HPLC method: Chiralpak IC column; mobile phase 95/5 hexane/EtOH; flow rate: 1.0 mL/min; detection wavelength $\lambda$=220 nm; $t_{major}$=11.02 min, $t_{minor}$=8.88 min.

Structure identification: $^1$H NMR (400 MHZ, DMSO-$d_6$) δ 10.19 (s, 1H), 7.62-7.55 (m, 2H), 7.49 (dd, J=4.3, 2.3 Hz, 4H), 7.41 (dd, J=8.5, 2.1 Hz, 1H), 7.09 (d, J=8.6 Hz, 1H), 4.76 (s, 1H), 1.61 (s, 3H), 1.30 (s, 9H). $^{13}$C NMR (101 MHz, DMSO-$d_6$) δ 176.7, 158.5, 146.1, 130.4, 129.9, 129.7, 129.1, 127.6, 127.5, 126.6, 123.4, 123.3, 109.9, 81.9, 62.9, 60.1, 34.8, 31.8, 12.4. HRMS (ESI-TOF) Calcd. for $C_{22}H_{22}N_2NaO_5S$ [M+Na]$^+$: 433.1192; found: 433.1181.

Example 12: Synthetic Compound I-la

Add 0.2 mmol of 2-nitrobenzofuran II-l, 0.26 mmol of 5H-thiazolone III-a, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is complete, the crude product is separated and purified by column chromatography to obtain compound I-la.

White solid; 94% yield; >20:1 dr, 91% ee; m.p. 156.9-157.7° C., $[\alpha]_D^{25}$=−285.5 (c 1.0, $CH_2Cl_2$).

Accordingly, the ee value is determined by HPLC method: Chiralpak IC column; mobile phase 95/5 hexane/$^i$PrOH; flow rate: 1.0 mL/min; detection wavelength $\lambda$=220 nm; $t_{major}$=32.45 min, $t_{minor}$=39.30 min.

Structure identification: $^1$H NMR (300 MHZ, DMSO-$d_6$) δ 10.22 (s, 1H), 7.58-7.45 (m, 5H), 7.33-7.22 (m, 2H), 4.85 (s, 1H), 3.87 (s, 3H), 1.59 (s, 3H). $^{13}$C NMR (101 MHz, DMSO-$d_6$) δ 176.6, 148.7, 144.4, 130.4, 130.0, 129.6, 129.1, 129.0, 127.6, 126.5, 124.8, 124.2, 118.0, 114.3, 82.0, 62.9, 60.5, 56.4, 12.4. HRMS (ESI-TOF) Calcd. for $C_{19}H_{15}{}^{79}BrN_2NaO_5S$ [M+Na]$^+$: 484.9777; found: 484.9764; For $C_{19}H_{15}{}^{81}BrN_2NaO_5S$ [M+Na]$^+$: 486.9757; found: 486.9739.

Example 13: Synthetic Compound I-ab

Add 0.2 mmol of 2-nitrobenzofuran II-a, 0.26 mmol of 5H-thiazolone III-b, 100 mg of 5A molecular sieve and 0.02 mmol of chiral catalyst D into a dry test tube. Then, add 2.0 mL of dichloromethane, wherein the reaction is carried out at room temperature under argon protection. After the reaction is completed, the crude product is separated and purified by column chromatography to obtain compound I-ab.

White solid; 60% yield; >20:1 dr, 89% ee; m.p. 160.7-161.5° C., $[\alpha]_D^{25}$=−171.5 (c 0.5, $CH_2Cl_2$).

Wherein, the ee value is determined by HPLC method: Chiralpak IC column; mobile phase 90/10 hexane/EtOH; flow rate: 1.0 mL/min; detection wavelength $\lambda$=220 nm; $t_{major}$=23.50 min, $t_{minor}$=14.23 min.

Structure identification: $^1$H NMR (300 MHz, DMSO-$d_6$) δ 10.05 (s, 1H), 7.56(dd, J=14.6, 7.4 Hz, 2H), 7.47 (d, J=7.7 Hz, 1H), 7.41-7.31 (m, 3H), 7.17-7.10 (m, 2H), 4.80 (s, 1H), 1.59 (s, 3H). $^{13}$C NMR (151 MHz, DMSO-$d_6$) δ 176.2, 160.6 (d, J=250.7 Hz, 1C), 160.5, 133.2 (d, J=9.1 Hz, 1C), 130.8, 130.4 (d, J=3.0 Hz, 1C), 126.5, 125.7, 125.2 (d, J=4.5 Hz, 1C), 123.7, 123.4, 117.2 (d, J=22.6 Hz, 1C), 116.5 (d, J=10.6 Hz. 1C), 110.7, 79.8 (d, J=3.0 Hz, 1C), 62.4, 59.9, 12.2. HRMS (ESI-TOF) Calcd. for $C_{18}H_{14}FN_2O_4S$ [M+H]$^+$: 373.0653; found: 373.0652.

Example 14: Synthetic Compound I-ac

Add 0.2 mmol of 2-nitrobenzofuran II-a, 0.26 mmol of 5H-thiazolone III-c, 100 mg of 5A molecular sieve and 0.02 mmol of chiral catalyst D into a dry test tube. Then, add 2.0 mL of dichloromethane, wherein the reaction is carried out at room temperature under argon protection. After the reaction is completed, the crude product is separated and purified by column chromatography to obtain compound I-ac.

White solid; 72% yield; >20:1 dr, 93% ee ; m.p. 173.4-174.1° C., $[\alpha]_D^{25}$=−64.2 (c 0.5, CH$_2$Cl$_2$).

Wherein, the ee value is determined by HPLC method: Chiralpak IC column; mobile phase 80/20 hexane/EtOH; flow rate: 1.0 mL/min; detection wavelength λ=220 nm; $t_{major}$=11.64 min, $t_{minor}$=16.50 min.

Structure identification: $^1$H NMR (300 MHz, DMSO-d$_6$) δ 10.16 (s, 1H), 7.53-7.44 (m, 3H), 7.43-7.35 (m, 1H), 7.20-7.11 (m, 2H), 7.06-7.01 (m, 2H), 4.79 (s, 1H), 1.58 (s, 3H). $^{13}$C NMR (151 MHz, DMSO-d$_6$) δ 176.6, 163.3 (d, J=249.2 Hz, 1C), 160.4, 130.8, 130.0 (d, J=9.1 Hz, 2C), 126.6, 126.2, 126.0 (d, J=3.0 Hz, 1C), 123.6, 123.5, 116.2 (d, J=22.6 Hz, 2C), 110.7, 81.3, 63.1, 59.8, 12.3. HRMS (ESI-TOF) Calcd. for C$_{18}$H$_{14}$FN$_2$O$_4$S [M+H]$^+$: 373.0653; found: 373.0662.

Example 15: Synthetic Compound I-ad

Add 0.2 mmol of 2-nitrobenzofuran II-a, 0.26 mmol of 5H-thiazolone III-d, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ad.

White solid; 78% yield; >20:1 dr, 98% ee; m.p. 186.0-186.7° C., $[\alpha]_D^{25}$=−389.3 (c 0.5, CH$_2$Cl$_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=13.93 min, $t_{minor}$=8.09 min.

Structure identification: $^1$H NMR (400 MHZ, DMSO-d$_6$) δ 10.25 (s, 1H), 7.66-7.56 (m, 4H), 7.53-7.46 (m, 1H), 7.45-7.37 (m, 1H), 7.22-7.12 (m, 2H), 4.85 (s, 1H), 1.60 (s, 3H). $^{13}$C NMR (101 MHZ, DMSO-d$_6$) δ 176.6, 160.5, 135.3, 130.9, 129.5, 129.2, 128.7, 126.6, 126.2, 123.6, 123.5, 110.8, 81.2, 63.1, 59.8, 12.3. HRMS (ESI-TOF) Calcd. for C$_{18}$H$_{14}$ClN$_2$O$_4$S [M+H]$^+$: 389.0357; found: 389.0364.

Example 16: Synthetic Compound I-ae

Add 0.2 mmol of 2-nitrobenzofuran II-a, 0.26 mmol of 5H-thiazolone III-e, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ae.

White solid; 72% yield; >20:1 dr, 96% ee; m.p. 175.7-176.6° C., $[\alpha]_D^{25}$=−37.8 (c 0.5, CH$_2$Cl$_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=11.44 min, $t_{minor}$=9.76 min.

Structure identification: $^1$H NMR (300 MHZ, DMSO-d$_6$) δ 10.25 (s, 1H), 7.79-7.67 (m, 2H), 7.58-7.45 (m, 3H), 7.44-7.35 (m, 1H), 7.22-7.08 (m, 2H), 4.84 (s, 1H), 1.59 (s, 3H). $^{13}$C NMR (75 MHz, DMSO-d$_6$) δ 176.4, 160.2, 131.9, 130.6, 129.4, 128.8, 126.3, 125.9, 123.8, 123.3, 123.2, 110.5, 81.0, 62.9, 59.5, 12.0. HRMS (ESI-TOF) Calcd. for C$_{18}$H$_{14}$$^{79}$BrN$_2$O$_4$S [M+H]$^+$: 432.9858; found: 432.9852; For C$_{18}$H$_{14}$$^{81}$BrN$_2$O$_4$S [M+H]$^+$: 434.9833; found: 434.9843.

Example 17: Synthetic Compound I-af

Add 0.2 mmol of 2-nitrobenzofuran II-a, 0.26 mmol of 5H-thiazolone III-f, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-af.

White solid; 75% yield; >20:1 dr, 90% ee; m.p. 224.0-224.8° C., $[\alpha]_D^{25}=-112.3$ (c 0.5, $CH_2Cl_2$).

Wherein, the ee value is determined by HPLC method: Chiralpak IC column; mobile phase 80/20 hexane/EtOH; flow rate: 1.0 mL/min; detection wavelength λ=220 nm; $t_{major}$=32.08 min, $t_{minor}$=17.18 min.

Structure identification: $^1$H NMR (300 MHZ, DMSO-$d_6$) δ 10.08 (s, 1H), 7.99-7.82 (m, 1H), 7.62-7.54 (m, 1H), 7.47 (d, J=7.1 Hz, 1H), 7.42-7.35 (m, 1H), 7.34-7.26 (m, 1H), 7.19-7.10 (m, 2H), 4.82 (s, 1H), 1.60 (s, 3H). $^{13}$C NMR (101 MHz, DMSO-$d_6$) δ 176.1, 160.5, 156.7 (d, J=253.5 Hz, 1C), 136.3, 130.9, 129.9, 126.6, 126.4 (d, J=4.0 Hz, 1C), 125.7, 123.6 (d, J=8.1 Hz, 1C), 118.5 (d, J=13.1 Hz, 1C), 110.8, 110.3 (d, J=22.2 Hz, 1C), 79.4, 79.4, 62.7, 59.9, 12.2. HRMS (ESI-TOF) Calcd. for $C_{18}H_{13}^{79}BrFN_2O_4S$ [M+H]$^+$: 450.9783; found: 450.9758; For $C_{18}H_{13}^{81}BrFN_2O_4S$ [M+H]$^+$: 452.9739; found: 452.9712.

Example 18: Synthetic Compound I-ag

Add 0.2 mmol of 2-nitrobenzofuran II-a, 0.26 mmol of 5H-thiazolone III-g, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ag.

Yellow solid; 83% yield; >20:1 dr, 81% ee; m.p. 134.3-135.1° C., $[\alpha]_D^{25}=-86.6$ (c 0.5, $CH_2Cl_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=24.80 min, $t_{minor}$=14.80 min.

Structure identification: $^1$H NMR (300 MHz, DMSO-$d_6$) δ 10.23 (s, 1H), 7.94-7.80 (m, 1H), 7.47 (d, J=7.5 Hz, 1H), 7.43-7.35 (m, 1H), 7.24-7.09 (m, 2H), 6.85 (d, J=3.5 Hz, 1H), 6.60 (dd, J=3.5, 1.8 Hz, 1H), 4.81 (s, 1H), 1.57 (s, 3H). $^{13}$C NMR (75 MHz, DMSO-$d_6$) δ 175.3, 160.2, 145.2, 142.3, 130.4, 126.1, 125.1, 123.1, 123.0, 111.4, 111.2, 110.4, 75.9, 63.1, 58.9, 11.9. HRMS (ESI-TOF) Calcd. for $C_{16}H_{12}N_2O_5S$ [M+Na]$^+$: 367.0359; found: 367.0360.

Example 19: Synthetic Compound I-ah

Add 0.2 mmol of 2-nitrobenzofuran II-a, 0.26 mmol of 5H-thiazolone III-h, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ah.

White solid; 75% yield; >20:1 dr, 80% ee; m.p. 221.9-222.7° C., $[\alpha]_D^{25}=-60.3$ (c 0.5, $CH_2Cl_2$).

Wherein, the ee value is determined by HPLC method: Chiralpak IC column; mobile phase 90/10 hexane/EtOH; flow rate: 1.0 mL/min; detection wavelength λ=220 nm; $t_{major}$=19.62 min, $t_{minor}$=16.90 min.

Structure identification: $^1$H NMR (400 MHZ, DMSO-$d_6$) δ 10.19 (s, 1H), 8.62-8.55 (m, 1H), 8.13-8.02 (m, 2H), 7.92-7.83 (m, 1H), 7.78-7.66 (m, 2H), 7.55-7.48 (m, 1H), 7.44-7.35 (m, 1H), 7.20-7.12 (m, 2H), 4.86 (s, 1H), 1.64 (s, 3H). $^{13}$C NMR (101 MHz, DMSO-$d_6$) δ 176.0, 160.6, 149.0, 146.8, 138.3, 131.2, 130.8, 129.5, 128.5, 128.4, 128.3, 126.6, 125.8, 123.7, 123.4, 119.9, 110.9, 83.4, 63.5, 60.0, 12.5. HRMS (ESI-TOF) Calcd. for $C_{21}H_{16}N_2O_4S_2$ [M+H]$^+$: 406.0856; found: 406.0864.

Example 20: Synthetic Compound I-ai

Add 0.2 mmol of 2-nitrobenzofuran II-a, 0.26 mmol of 5H-thiazolone III-i, 100 mg of 5A molecular sieve and 0.02 mmol of chiral catalyst D into a dry test tube. Then, add 2.0 mL of dichloromethane, wherein the reaction is carried out at room temperature under the argon protection. After the reaction is completed, the crude product is separated and purified by column chromatography to obtain compound I-ai.

White solid; 70% yield; >20:1 dr, 82% ee; m.p. 182.6-183.5° C., $[\alpha]_D^{25}=-113.2$ (c 0.5, $CH_2Cl_2$).

Wherein, the ee value is determined by HPLC method: Chiralpak IC column; mobile phase 90/10 hexane/EtOH;

flow rate: 1.0 mL/min; detection wavelength λ=220 nm; $t_{major}$=35.00 min, $t_{minor}$=28.40 min.

Structure identification: $^1$H NMR (300 MHz, DMSO-d$_6$) δ 10.14 (s, 1H), 8.69-8.61 (m, 1H), 8.05-7.93 (m, 1H), 7.56 (dd, J=8.2, 4.2 Hz, 2H), 7.47 (d, J=7.5 Hz, 1H), 7.42-7.31 (m, 1H), 7.13 (dd, J=8.0, 5.7 Hz, 2H), 4.77 (s, 1H), 1.59 (s, 3H). $^{13}$C NMR (101 MHz, DMSO-d$_6$) δ 176.2, 160.6, 149.6, 148.5, 137.9, 130.7, 126.5, 125.7, 125.6, 123.8, 123.3, 123.0, 110.8, 83.5, 62.9, 60.1, 12.4. HRMS (ESI-TOF) Calcd. for C$_{17}$H$_{14}$N$_3$O$_4$S [M+H]$^+$: 356.0700; found: 356.0694.

The embodiments of the present invention as described above is exemplary only and not intended to be limiting the present invention. All modifications, equivalent replacements and improvements made within the spirit and scope of the present invention shall be encompassed in the protection scope of the present invention.

What is claimed is:

1. A 1,4-sulfur-bridged polycyclic compounds containing a dihydrobenzofuran structure, characterized in that, having a structural formula (I) as follows:

in the above structure formula, Ar is one of substituted aromatic rings and heteroaromatic rings, wherein R$^1$ group is a single substituent or a multi-substituted group, wherein the substituent is selected from a group consisting of hydrogen, alkyl, alkoxy, nitro and halogen, wherein R$^2$ group is selected from a group consisting of methyl, ethyl and benzyl.

2. A preparation method of 1,4-sulfur-bridged polycyclic compounds containing a dihydrobenzofuran structure according to claim 1, characterized in that:

dissolving 2-nitrobenzofuran (II) and 5H-thiazolone (III) in an organic solvent;
then adding molecular sieve and chiral catalyst;
stirring and allowing reaction at room temperature under argon protection; and
carrying out separation and purification after the reaction is completed to obtain a 1,4-sulfur-bridged polycyclic compound (I) containing dihydrobenzofuran structure, wherein the 2-nitrobenzofuran (II) has a structure as follows:

the 5H-thiazolone (III) has a structure as follows:

3. The preparation method according to claim 2, characterized in that: the organic solvent is selected from a group consisting of one or a mixture of: toluene, mesitylene, dichloromethane, chloroform, tetrahydrofuran, ether, acetonitrile, ethanol, methanol, 1,4-dioxane, and chlorobenzene.

4. The preparation method according to claim 3, characterized in that: the organic solvent is dichloromethane.

5. The preparation method according to claim 2, characterized in that: the chiral catalyst is a chiral tertiary amine-thiourea bifunctional catalyst or a chiral tertiary amine-squaramide bifunctional catalyst.

6. The preparation method according to claim 2, characterized in that: the molar ratio of the reaction substrate is $n_{II}:n_{III}$=2:1~1:2.

7. The preparation method according to claim 6, characterized in that: the molar ratio of the reaction substrate is $n_{II}:n_{III}$=1:1.3.

8. The 1,4-sulfur-bridged polycyclic compounds containing a dihydrobenzofuran structure according to claim 1, wherein the 1,4-sulfur-bridged polycyclic compounds containing a dihydrobenzofuran structure is prepared into an antitumor medicament having inhibitory effect on human leukemia cell K562 and human lung cancer cell A549.

* * * * *